United States Patent
Hockaday et al.

(10) Patent No.: US 7,320,261 B1
(45) Date of Patent: Jan. 22, 2008

(54) ANIMAL SKIN AND EYE MOISTURE AND HEAT SIMULATOR

(75) Inventors: Robert G. Hockaday, Los Alamos, NM (US); Patrick S. Turner, Los Alamos, NM (US); Marc D. DeJohn, Los Alamos, NM (US)

(73) Assignee: Arena Industries, LLC, Irvine, CA (US)

( * ) Notice: Subject to any disclaimer, the term of this patent is extended or adjusted under 35 U.S.C. 154(b) by 188 days.

(21) Appl. No.: 11/036,388

(22) Filed: Jan. 18, 2005

Related U.S. Application Data

(60) Provisional application No. 60/536,515, filed on Jan. 15, 2004.

(51) Int. Cl.
*G01N 17/00* (2006.01)
(52) U.S. Cl. .................... 73/865.9; 73/865.6
(58) Field of Classification Search .............. 73/38, 73/865.9, 865.6, 866, 73, 74; 374/41, 141, 374/142
See application file for complete search history.

(56) References Cited

U.S. PATENT DOCUMENTS

| | | | |
|---|---|---|---|
| 4,341,832 A * | 7/1982 | Barnett et al. .............. | 428/196 |
| 4,622,852 A * | 11/1986 | James et al. ............... | 73/865.6 |
| 5,452,480 A | 9/1995 | Ryden | |
| 5,652,965 A | 8/1997 | Crooks | |
| 5,749,259 A | 5/1998 | Hamouda et al. | |
| 5,846,650 A | 12/1998 | Ko et al. | |
| 6,196,409 B1 * | 3/2001 | Lake et al. .................. | 220/371 |
| 6,487,891 B2 * | 12/2002 | Moretti ........................... | 73/38 |
| 6,524,488 B1 * | 2/2003 | Insley et al. ................. | 210/767 |
| 6,546,285 B1 | 4/2003 | Owen et al. | |
| 6,548,134 B1 * | 4/2003 | Rogers ....................... | 428/35.7 |
| 6,805,124 B2 * | 10/2004 | Japuntich et al. ....... | 128/206.15 |
| 6,904,820 B2 * | 6/2005 | Tate et al. ..................... | 73/866 |

OTHER PUBLICATIONS

ASTM International; *Standard Specification for Skier Goggles and Faceshields (F659-98)*; Published Aug. 1998 by ASTM International, 100 Barr Harbor Drive, PO Box C700, West Conshohocken, PA 19428-2959; pp. 1-8.

* cited by examiner

*Primary Examiner—Robert Raevis*
(74) *Attorney, Agent, or Firm*—Pepper Hamilton LLP

(57) ABSTRACT

A new simulator of the human head and animal bodies mimics moisture transpiration from eyes and skin and heat emission. The present invention used to demonstrate and quantify anti-fogging performance of goggles and apparel. Thin water permeable membranes are mounted onto a container containing a thermostatically controlled, heated and stirred reservoir of water as a simulation of the moisture source of the human eyes and skin. A light source and optical mesh patterns help illuminate water condensation on the inner lens of the goggles. The simulator results in a reliable and convenient demonstration and testing system for moisture condensation in goggle lenses, and heat and moisture apparel.

10 Claims, 9 Drawing Sheets

ANIMAL SKIN AND EYE MOISTURE AND HEAT SIMULATOR

This application claims the benefit of U.S. Provisional Patent Application No. 60/536,515, filed Jan. 15, 2004.

BACKGROUND OF THE INVENTION

A fogging problem with sport goggle lenses has existed for many years. In snow ski goggles this effect occurs when the interior surface of the lens reaches the dew point. Problems are caused by a combination of cooling of the lens due to contact with cold air, and the flow of moisture into the goggle interior air volume from the face. Air is drawn into the lens-face volume. The air is heated by contact with the face, air filters, and the lens, and causes a drop in relative humidity. The air absorbs water vapor and can flow out of the lens-face volume. If there is sufficient airflow through the goggles, then the lenses can be kept clear of condensing water vapor.

The previous standard, ASTM standard F 659-98, used a water bath heated to 50° C., a circulation fan, and placed the goggle lens between the humidified air and the room air. The previous standard test was designed to test lens coatings and quantified the anti-fogging properties by the time optical obscuration occurred. This test did not address airflow conditions of a goggle when worn on a human face, or steady operation conditions.

PRIOR ART

Ryden (U.S. Pat. No. 5,452,480) placed goggles on humans and conducted tests located on ski hills with hygrometer and thermometer logging instruments in the eye lens space. Ryden also conducted a test in which a goggle was placed over a dish of water with a 2.5 cm diameter kept at 130° F. Ryden also conducted a time test with the fan-ventilated goggle to go from 100% relative humidity to 60% relative humidity. Ryden also conducted a goggle comparison test with chilled goggles that were then placed on a human face and the fogging and clearing was observed. Differences in fogging time were compared between goggles.

Crooks (U.S. Pat. No. 5,652,965) tested goggles on humans while snow skiing. Weather conditions were noted and observations of fogging or non-fogging of the goggle lenses.

Hanouda (U.S. Pat. No. 5,749,259) references prior art in simulating sweating human skin with wicking materials and water wicking sintered metal plates for testing fabrics. Hanouda adds to the technique of the heated water wicking plate that controls of constant power and water flux to simulate human skin to test fabrics. Water vapors passing only through membranes are not used and a sintered metal plate moisture source is oriented horizontally on a leveling stand. The pores in the sintered metal and paper layers are 20 microns in diameter. Thus, the sweating hot plate would not be suitable for use as a uniform moisture source vertically oriented to simulate thermal convection from vertically oriented surfaces such as a human face or body. This is because if the wicking plate were vertically oriented it would be expected to leak water at the lower edge and be dryer on the upper edge of the porous metal plate due to the gravitationally induced pressure difference between the bottom and the top of the porous metal plate.

Ko et al. (U.S. Pat. No. 5,846,650) fog tested coatings on samples that were passed through a steam source of boiling deionized water for 1 second. Ko observed the light transmission through the samples with wavelengths from 550 nm to 750 nm. Water vapor only passing membranes was not used and they did not simulate continuous operation conditions.

Owen et al. (U.S. Pat. No. 6,546,285) performed skin adhesion tests for various time periods of contact for sensors on humans. The simulator was an electrical simulation of the human body. This patent describes hydro gels and silicone gels and chemical compounds for long-term compatibility on the surface of the skin. The water permeability and compatibility with human skin is also mentioned.

ASTM Standard F 659-98 is a standard goggle lens anti-fogging coatings test. Placing the items to be tested over a moisture source tests standard goggle lenses and anti-fogging coatings. A laser light is used to define fogging by light obscuration. This is a timed test. It is mentioned that there is not a test available for ventilation and air flow in goggles.

No human shaped simulator or vertical surface exists for testing of apparel. No simulators exist that achieve a steady state condition for goggles that maintain constant heat, air, and moisture flows.

Needs exist for a simulator to test and quantify different techniques to reduce fogging on goggle lenses.

SUMMARY OF THE INVENTION

The present invention is a simulator of the human face that easily produces fogging of goggle lenses and also allows for quantitative comparisons between different fog reducing techniques. A critical parameter in the reduction of fogging is convective airflow through vents and the interior space between the lens face and the face. The simulator of the present invention is portable and may be operated in freezers to simulate winter and arctic conditions. The simulator may be placed in an environmental mock-up chamber where temperature, humidity, airflow, rain, mist, dust, snow and other environmental conditions affecting the goggles is controlled. The simulator may also be operated in such a way that the moisture delivery rates and temperature differences mimic a human or animal from a resting state to normal transpiration and beyond to the extreme moisture delivery rates.

Generally, a human emits moisture at rates between approximately 0.076 g/hr (resting) and approximately 1.8 g/hr (strenuous exercise) over the surface of the facial area of approximately 68 cm$^2$, including the eyes. This translates to between about 270 g/m$^2$*day to about 6400 g/m$^2$*day. Body skin typically will emit moisture at a rate of approximately 300 to 1500 g/m$^2$/day (See U.S. Pat. No. 6,546,285). To be effective, goggles must remove this moisture by airflow through the goggle, diffused out, wicked off, or absorbed by the goggle system. To simulate a human face, the surface of the simulator must be at a body temperature above the surrounding air and deliver between about 0.021 mg/cm$^2$*sec and about 0.50 mg/cm$^2$*sec of water.

As a refinement the simulation of the eye area should be near 100% relative humidity. A saline solution that matches the surface vapor pressure of human skin and eyes may also be used. In many tests, the objective is to create fogging conditions and achieve contrast between different anti-fogging techniques in goggles. Therefore, tests are performed where the internal temperatures are as high as about 50° C. with surrounding air at approximately 20° C. and about 30% relative humidity. The moisture delivery rate is generally higher than what a human skin and eyes can produce and the air can carry additional moisture. Thus, these conditions produce accelerated fogging on goggle lenses.

From tests it is found that the amount of goggle fogging on a lens surface may be quantified as a percentage of the lens surface. A plot of data showing the amount of fogging compared to the predicted flow rate may be produced. A simple mathematical model of airflow and heat transfer of conduction, convection, evaporation, and radiation is constructed to predict airflow and maximum moisture removal rates. The airflow model is then compared to the experimental data of a variety of goggle styles that are modified with different air channel dimensions and open cell foams. A correlation between the model and the data is then obtained. The general objective is to have a goggle lens that is less than about 10% fogged. To accomplish this, a flow rate higher than approximately 1 liter/minute is required.

A goggle comparator simulates two human faces under the same conditions. In a preferred embodiment the goggles should be located side by side. This ensures that conditions for each goggle are exactly the same during tests. However, in other embodiments, for ease of construction, the simulator is built with a single tube placing goggles vertically, with some separation between the simulated face positions to mitigate the effects of moisture and convective airflow interference between the goggles. Other designs to avoid these effects include two tubes side by side with a common water circulation flow.

If the relative humidity of the outside air is high, raising the temperature of the incoming air to the goggle is needed for the airflow to carry heat and moisture from the lens-face volume to the outside surrounding air. Heat is transferred to the goggle where it makes contact with skin and transfers heat into the airflow through the goggle vents, frame, and lenses. The face and eyes also radiate heat to the inner lens, filter, and frame of the goggle.

In order to overcome the shortcomings previously described, the present invention is a device that combines several components and optimizes physical functions in order to achieve the desired effect.

Using membranes achieves uniform moisture delivery rates per unit area in the range of about 270 g/m$^2$*day to about 12,000 g/m$^2$*day. Thermal conductivity is similar to human skin, approximately 0.60 W/m*K. Vertical surface orientation and dimensions simulate human or animal transpiration surfaces. Emissivity is similar to human skin or water. Surface temperatures are similar to a human face (about 92° F.). Eye areas simulate the wet surfaces of eyes. The water on the simulated skin and eyes has a salt content similar to various sweat and eye fluids, or has similar water vapor pressures. Witness surfaces are used to quantify how much dust or particles reach the surfaces inside the goggles.

Goggles are used in a wide range of extreme conditions. Often goggle wearers experience these extreme conditions while heavily exerting themselves. Some of these conditions and goggle types include:

In typical snow skiing conditions the air outside the goggles is near or below the freezing point of water. Snow may be falling and the relative humidity may be 100%.

In cool to hot, dry (about 49° C., relative humidity below about 20%), dusty environment particles range from grains of sand sub millimeter scale to sub micron. Examples of this type of goggle include those used by police, military, firefighters, medical workers, and construction workers.

In hot, moist (about 30° C., relative humidity above about 80%) environments, goggles are used for simulated ammunition exercises (paint ball), for police, military, and construction work.

In mountain climbing and arctic exploration, very cold temperatures are encountered with dew points of about 40° C. and about 100% relative humidity.

The simulator is also used to simulate human or animal skin surfaces to test, compare, and demonstrate the performance of clothing, heat, moisture removal products, protective body covers, and enclosures.

Membrane surface layers are used to capture dust, viruses, and bacteria to observe the simulated efficacy of the apparel. Electret membranes and surfaces may be used to act as particle attractors. Additionally, sticky adhesive surfaces exposed to the interior air can be used to capture and hold particles.

These and further and other objects and features of the invention are apparent in the disclosure, which includes the above and ongoing written specification, with the drawings.

DETAILED DESCRIPTION OF THE PREFERRED EMBODIMENTS

Figure 1:
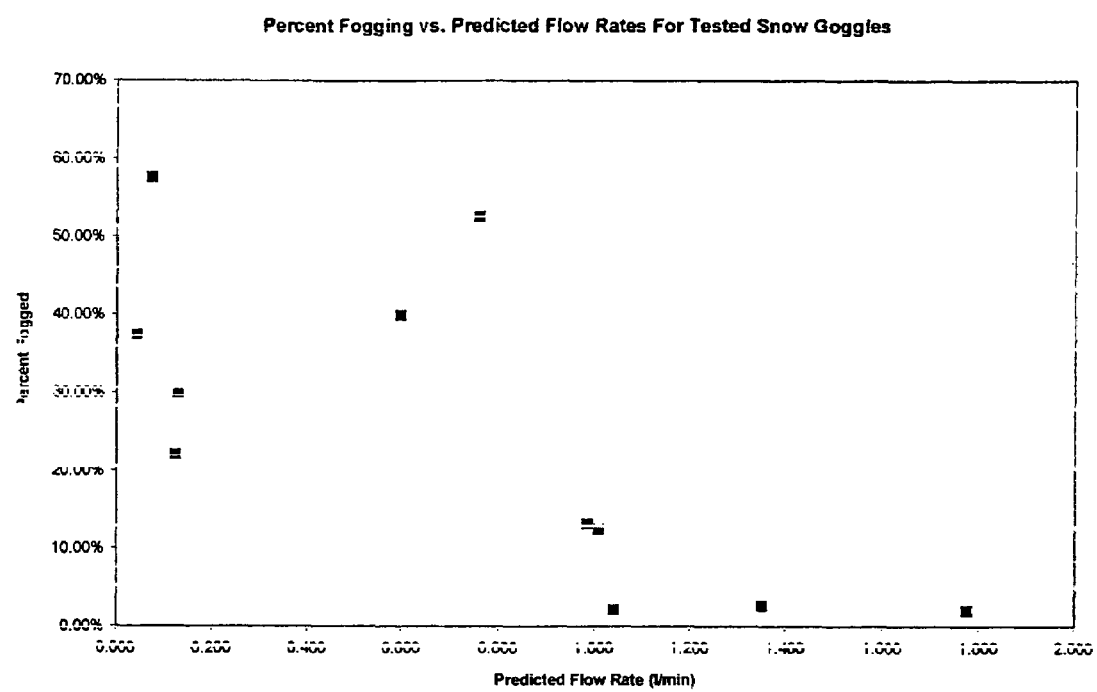
FIG. 1 is a graph of data showing the amount of fogging compared to predicted flow rate.

FIG. 1 is a plot of data showing the amount of fogging compared to the predicted flow rate. A simple mathematical model of airflow and heat transfer of conduction, convection, evaporation, and radiation is constructed to predict airflow and maximum moisture removal rates. The airflow model is then compared to the experimental data of a variety of goggle styles that are modified with different air channel dimensions and open cell foams. A correlation between the model and the data is then obtained. The general objective is to have a goggle lens that is less than about 10% fogged, and to accomplish this a flow rate higher than approximately 1 liter/minute is sufficient and is required.

Figure 2:
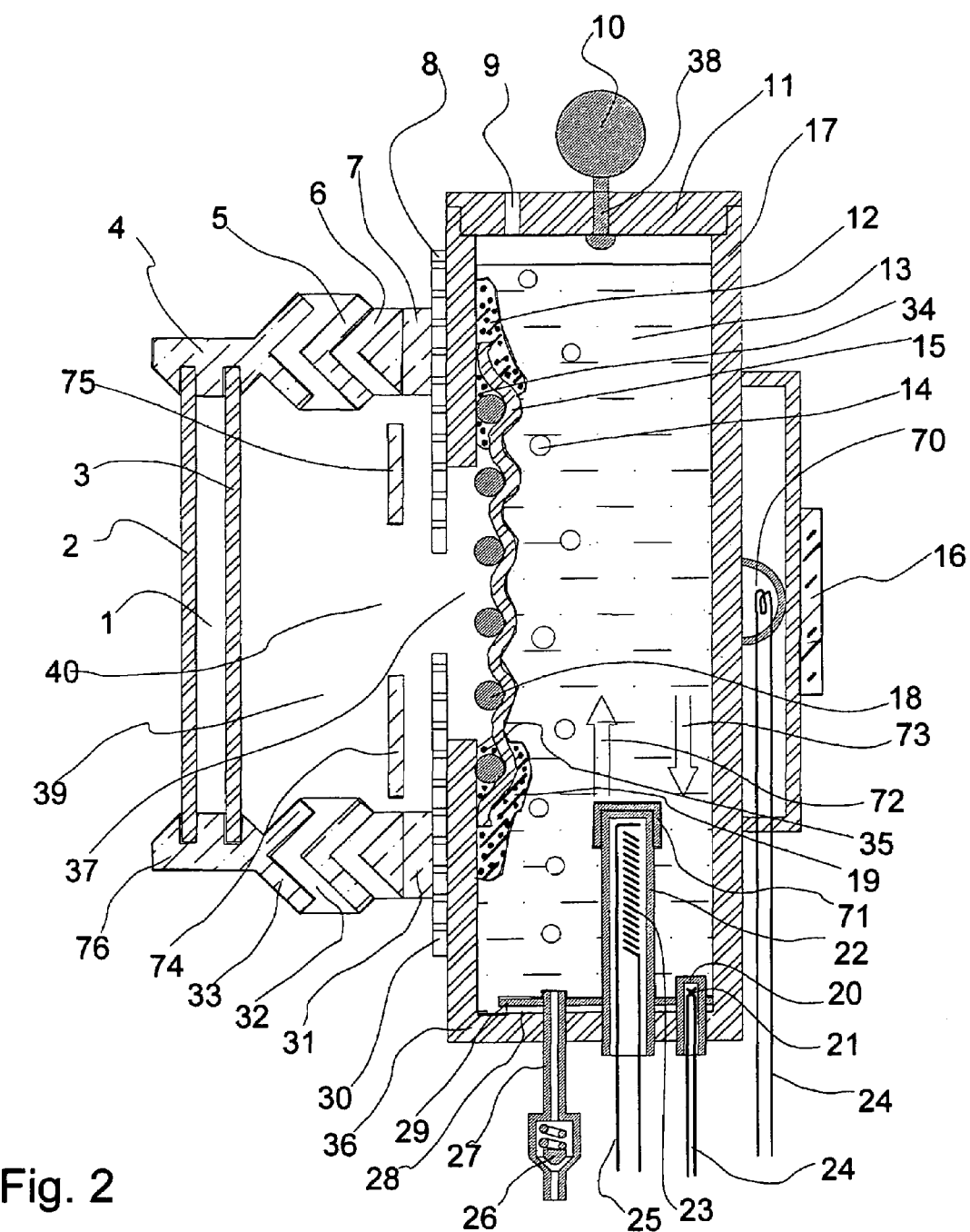
FIG. 2 is a cross-sectional view of a body simulator with goggles attached.

FIG. 2 shows a cross sectional view of a body simulator and attached goggles. The simulator consists of a six-inch diameter Plexiglas tube 17 with a Plexiglas base plate 36 welded to the bottom of the tube 17. A port aperture 37 is cut out of the Plexiglas tube 17 that roughly matches the area inside that of the goggle frame 4 or goggle gasket 7. Two or more port apertures 37 have multiple test points along the tube 17. At least six inches of space between the port apertures 37 is used to avoid interactions between goggles being tested.

A lid 11 is formed out of Plexiglas sheet to fit into the top end of the Plexiglas tube 17, for example, but not limited to, six inches in diameter and twenty-four inches tall. A lid handle 10 is attached to the lid with a screw 38. A vent hole 9 in the top of the lid is used to let air out of the interior of the Plexiglas tube 17.

A water vapor permeable and liquid water impermeable or liquid retaining membrane 15, such as twenty-five micrometer thick polyester urethane membrane (Stevens Urethane, 412 Main Street, Easthampton, Mass. 01027), or silicone rubber membrane thirty micrometer thick (Mitsubishi Plastics, Japan), or porous PTFE (Polytetrafluroethylene) hydrophobic membrane (Corning Costar Corporation, one Alewife Center, Cambridge, Mass., 02140), is cut to cover the aperture 37 as a rectangle about three inches by about six inches. Other suitable membrane materials include cellulose nitrate, cellulose acetate, porous PTFE, porous polyethylene, porous polypropylene, perfluoronated ion exchange polymer electrolyte NAFION (Solution Technology, Inc., PO Box 171, Mendenhall, Pa. 19357), sulfonated styrene-(ethylene-butylene)-sulfonated styrene, porous alumina, porous clays, small pore membranes that have been treated to be hydrophobic, dialysis membranes and ion exchange resin membranes (typically used in water purification, body contact products, batteries, fuel cells, reverses osmosis cells, and electrolysis cells). Porous metals that have small enough pores and have been treated with a coating, such as polytetrafluroethylene coated Raney nickel, not allowing liquid water to traverse or flow through the porous metal, or a porous metal film may also be suitable.

In FIG. 2 an electrical heater element 23 is placed inside the Plexiglas tube with a protective copper tube 22 that is solder sealed at the top with a copper tube cap 71. The copper tube is soldered to a copper sheet 29. A thermocouple protective tube 20 and an air entrance tube 27 are also soldered into the copper sheet 29. A Plexiglas base plate 36 is solvent (for example, methyl ethyl ketone (MEK)) welded to the Plexiglas tube 17. Holes are drilled in the base plate 36 to permit the copper tubing to be inserted through. The copper tubing 27, 22, 20, and the copper plate 29, are inserted from the inside of the Plexiglas tube 17 and sealed to the bottom of the Plexiglas tube with a silicone sealant 28 (for example, GE 100% silicone sealant, GE Sealants & Adhesives, Huntersville, N.C., 28078). The wide base of copper sheet 29 serves as a broad seal area and also dissipates the heat from the heater tube 22 before it can cause melting of the Plexiglas tube, especially if water is removed accidentally from the Plexiglas tube 17.

In operation, a thermocouple 24 is used with a thermostat electrical control system (for example, Omega CN 1632 DIN Temperature Controller, Omega Engineering, Inc., P.O. Box 2284 Stamford Conn. 06906-0284), which senses the temperature is below a set point and closes a switch. A switch closing from a controller (see 51 in FIG. 3) allows current to flow through the resistance element heater 23 and drive an air pump (see 58, 57, 56, 55, 54, in FIG. 3). The resistance element heater 23 heats the protective copper tube 22 and the water 13 around the copper tube 22. The air bubbles 14 from the pump flows though a check valve 26 and into the water 13 in the Plexiglas tube 17 to stir the warmed water 13 throughout the Plexiglas tube 17.

Figure 3:
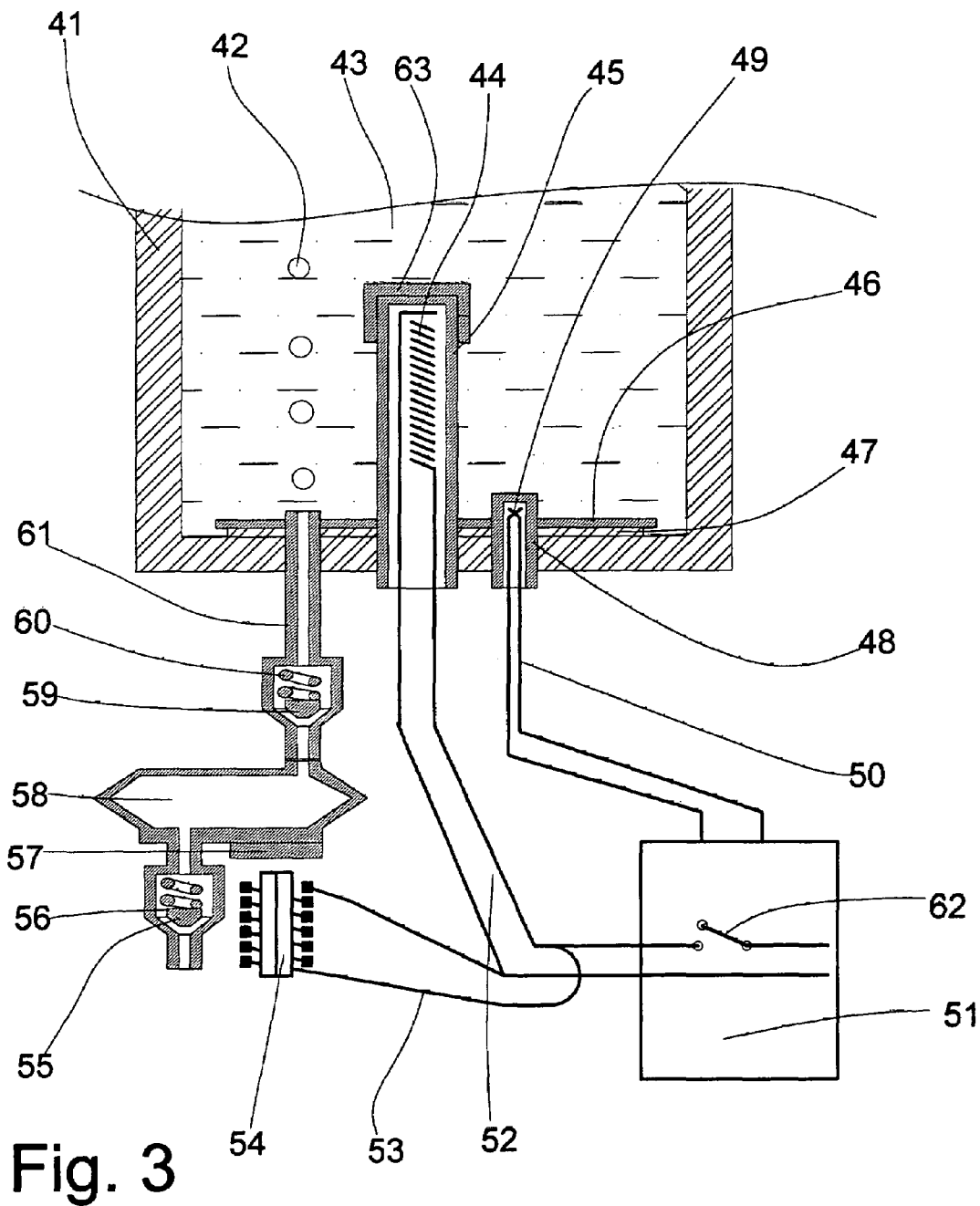
FIG. 3 is a cross-sectional view of a bottom of a Plexiglas tube and a control system.

When the temperature rises above the set point of the thermostat (see 51 in FIG. 3) in the water 13 sensed by the thermocouple 24, the switch (see 62 in FIG. 3) is opened in the thermostat controller (see 51 in FIG. 3). With the switch open (see 62 in FIG. 2) current though the electrical resistance heater ceases and the air pump (see 58, 57, 56, 55, 54, in FIG. 3) stops and the rising bubble 14 stirring stops. The check valve 26 in the airline stops water 13 from flowing back into the air pump (see 58, 57, 56, 55, 54, in FIG. 3).

Natural thermal convection also occurs from the water heated 13 by the electrical resistance heater 23 being buoyant and rising to the top of the water 13 in the Plexiglas tube 17. Cold water 73 sinks down along the perimeter of the Plexiglas tube 17 to the bottom of the Plexiglas tube 17 replacing the warm water 72 that had risen to the top of the Plexiglas tube. A vent hole 9 is provided in the top of the tube lid 11 to allow air from the pump to vent from the Plexiglas tube 17.

In FIG. 2 goggles are shown schematically as a cross section attached to the Plexiglas tube 17 around the port aperture 37. The goggles are strapped onto the Plexiglas tube 17 with the head strap of the goggle 16. To throttle and moderate the moisture flux from the membrane into the lens-face cavity a porous hydrophobic membrane 8, 30 such as 50 micrometer thick 1 micrometer diameter pore porous polypropylene (for example, Exxon Mobil Corporation, 5959 Las Colinas Bld., Irving, Tex., 75039-2298) is placed over the port aperture 37.

To simulate the spatial eye and skin differences in humid emissions, eyeholes 40 are cut in the porous membrane 8, 30. By varying the eyehole 40 diameters and the number and porosity of the porous hydrophobic membrane 8, 30 different moisture delivery rates and spatial distributions can be achieved. Hydrophilic membranes tend to absorb and hold moisture, thus they can be a transient source of water vapor that can interfere with observed fogging on the goggle inner lens 3.

The goggle shown in FIG. 2 shows the principal components of a frame 4, 73 face contact gasket 31, 7 air inlet and baffles 32, 33 inner and outer lens 3, 2, upper air vent channel 6 and baffle 5 and the face contact gasket 7, 31. In operation air will flow into the lower vent channel 32 absorb heat as it passes though the vent. The hot air rises past the simulated face 30, 8, 40 and the inner lens 3. The air will absorb moisture and heat from the simulated face 30, 8, and 40 in the lens face volume. The air will exit through the top of the goggle 6.

To simulate the heat and moisture transfer that occurs in goggles on human faces the following exemplary processes, but not limited to, are simulated:

Thermal conduction, from the face into the face gasket.

Diffusion of moisture from the face into the face lens volume.

Conduction and convection of heat from the face into the face lens volume.

Radiation from the face to the inner lens surface and the surrounding goggle frame.

Water or saline solution added to the surface beneath the face gasket to simulate sweat, rain, or snow.

Snow, rain, and dust can be sprayed or blown into the goggles to simulate various weather conditions.

The simulator can be placed inside an environmental chamber that simulates the expected weather and operating conditions.

When conduction simulations and tests are performed, preferably a variety of sensors are used to observe the conditions under which goggles are operational. Thermocouple and thermistor sensors are preferably placed in the water 13 of the Plexiglas tube 17; on the surface of the porous membrane 30, 8; between the contact gasket 7, 31 and the Plexiglas tube 17; between the contact gasket 31, 6 and baffles 33, 5; at the entrance and exit of the inlet air flow channels 32, 6; on the surface of the lenses 3, 2 in the inner lens air gap 1; and spatially positioned across the lenses 3, 2 to observe temperatures where water condenses; inside the inlet air flow channels 33; on the top vent channels 6; at the frame gasket interface 4, 76; and at the face gasket 7, 31. Plexiglas 17 surface interface.

Sticky glue-covered films, water absorption films, or film electret coupons 74, 75 may be used to sample particulates such as dirt, water droplets, salt, snow, bacteria, and viruses that enter the eye-lens volume. The film is placed inside 74 and outside 75 the goggles. These coupons 74, 75 may also be used to sample the source rate and many points inside the goggles to establish performance. The coupons 74, 75 are examined under a microscope, weighed, and a quantitative counting of particulates' accumulation is assessed.

Small cellulose sponges or water absorbents as coupons 74, 75 are used to obtain collected water that condenses or is propelled into the eye lens face volume. The sponge 74, 75 is weighed before and after at timed interval tests. To determine the moisture source rate from the simulator and humans, an unventilated goggle chilled to approximately 5° C. is used. The mass of condensed moisture is measured before and after being placed on the human face. The mass is measured by weighing the goggles before and after they are placed on the human face. The dew point is below about 5° C. in the surrounding air to avoid condensation from the outside air.

Features that may be used to simulate a human or animal subject more accurately include use of materials that more closely match the emissivity of the skin, eyes, and face. Small hydrometers located inside and outside the goggles assess the conditions occurring in the goggles.

To assess the fogging of the goggles, a light source 70 is mounted on the back of the Plexiglas tube 17 to illuminate the membrane assembly and the goggles lenses 2, 3. The support mesh 18 acts as a resolution pattern to increase visibility of the condensed water on the inner lens 3. The porous throttling membrane 8, 30 may also have detailed patterns on it to act as a resolution pattern. Lights may also be placed outside the goggle to illuminate the inner lens at low grazing angles to the inner lens. The amount of fogging is mapped with scales, grids, imaged with digital or film cameras, and quantified as a percentage area of the lens covered in condensed water.

FIG. 3 shows a cross sectional view of the bottom of the Plexiglas tube 41 and the control system. At the bottom of the tube there are three copper or brass tubes 61, 45, 48 soldered to a copper disk 46. The brass tube for the electrical resistance element is solder capped with a copper cap 63 and soldered to the copper plate 46. The electrical resistance element 44 slip fits into the brass tube 45.

A silicone sealant on the heater element is used to ensure good thermal contact with the brass tube 45 and the heater element 44, and is secured in the brass tube 45. The electrical connections go from the electrical resistance element 44 to a thermostat control system 51 (for example, Omega CN 1632 DIN Temperature Controller, Omega Engineering, Inc., P.O. Box, 2284 Stamford, Conn., 06906-0284).

A $\frac{1}{16}$-inch diameter brass tube 48 is placed in the copper base plate 46, 0.5 inches from the perimeter of the copper plate 46. This brass tube 48 goes 0.5 inches above the copper plate 46 and is sealed at the end and also to soldered to the copper plate 46. A type T (copper-constantan) thermocouple junction is sealed into the $\frac{1}{16}$ diameter copper tube 48 with silicone sealant.

A $\frac{1}{8}$-inch diameter copper tube 61 is placed into the copper plate 46 to provide the air inlet. Air bubbles are shown rising in the Plexiglas tube to stir the water. The copper plate 46 is sealed to the Plexiglas base plate 64 with a silicone sealant 47.

Also shown in FIG. 2 is a schematic representation of an air pump with a check valve 59 with a spring 60 to prevent back water flow, a diaphragm bellows 58, an inlet valve 55 and spring 56, a magnetic plate 57, and an electrical coil 54. The alternating current wiring 53, 52 to the air pump coil 54 and resistance heater element 44 are schematically running from a switch 62 in the thermostat controller 51.

In operation the thermocouple junction is wired 50 to the thermostat controller 51 and the thermostat will operate the switch 62 to the heater element 44 and air pump coil 54 to maintain a constant temperature in water 43 in the Plexiglas tube 44.

Figure 4:
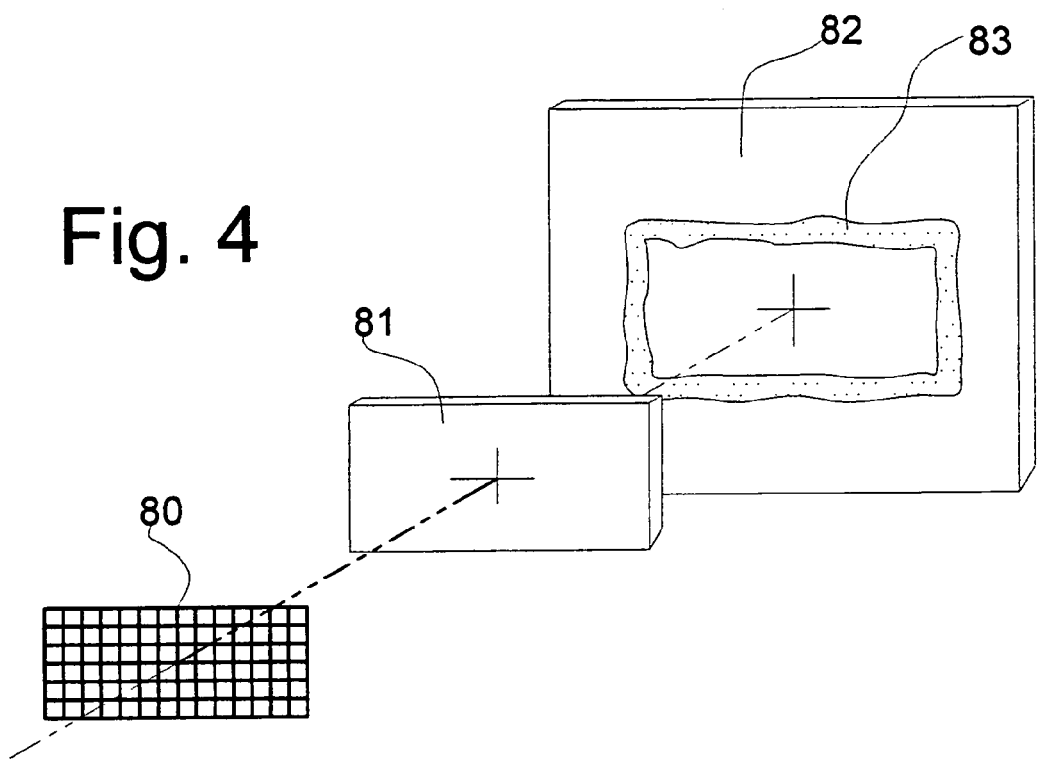
FIG. 4 is a perspective view of a water permeable membrane mounting assembly.

FIG. 4 shows the construction and mounting of a water permeable membrane. A water vapor permeable liquid water retaining membrane such as, but not limited to, 25-micrometer thick polyester urethane membrane 81 is cut, for example, into a rectangle 2.75 inches by 5.75 inches. A plastic coated fiberglass screen mesh (for example, McMaster-Carr, 9630 Norwalk Blvd., Santa Fe Springs, Calif., 90670-2932), is cut to be about $\frac{1}{8}$ of an inch smaller rectangle than the urethane membrane, approximately 2.5 inches by approximately 5.5 inches.

A bead of a silicone sealant 83, about $\frac{1}{8}$-inch in diameter is placed, for example, on a three inch by six-inch rectangular mark on an approximately 0.002-inch thick polyethylene membrane 82. The urethane membrane 81 is then placed on top of the silicone sealant 83 with the silicone sealant framing the urethane membrane 81. And the plastic coated mesh 80 is placed on top of the urethane membrane 81.

Figure 5:
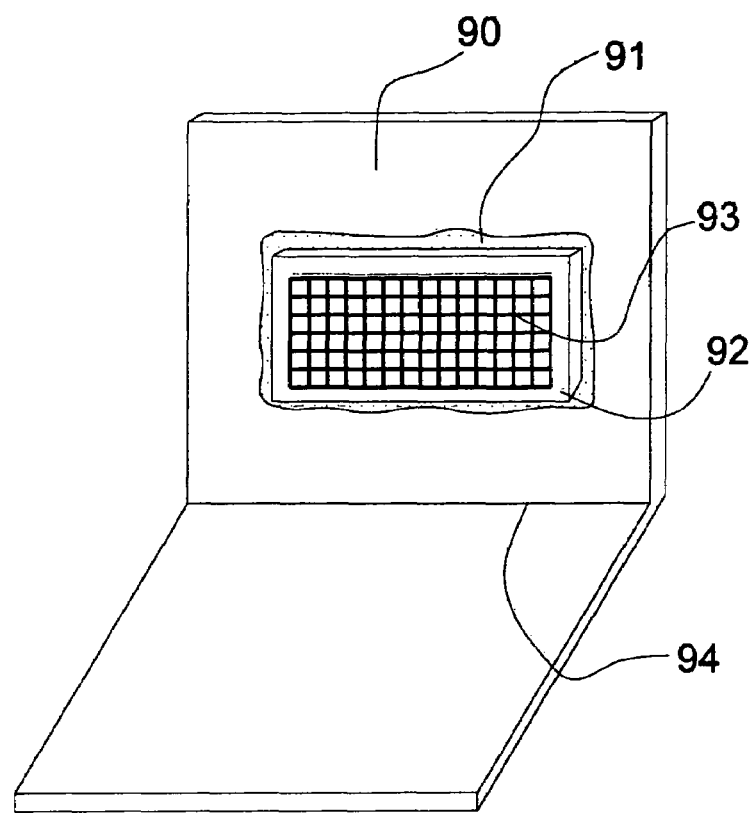
FIG. 5 is a perspective view of a silicone sealant on the membrane assembly of FIG. 4.

FIG. 5 shows a second roughly $\frac{1}{8}$-inch diameter bead of a silicone sealant 91 is placed on the edge of the urethane membrane 92. The screen mesh 93 is resting over the urethane membrane 92 and is framed by the silicone sealant bead 91. The polyethylene membrane 90 is then folded 94 over the assembly 91, 92, 93.

Figure 6:
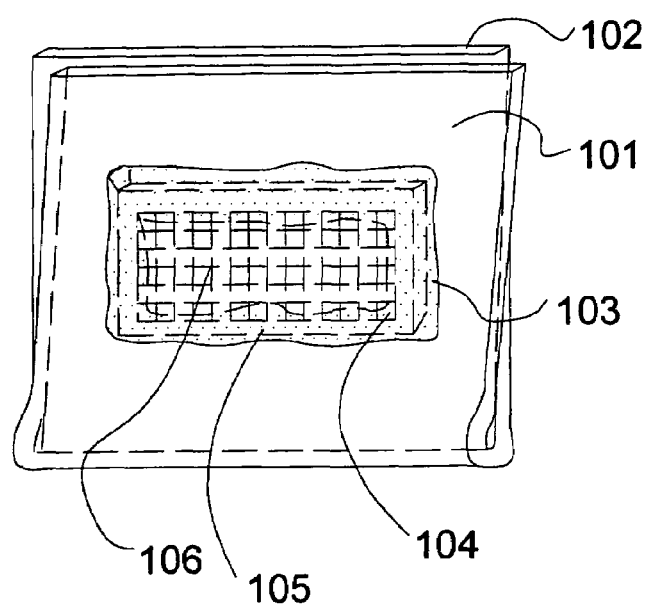
FIG. 6 is a sandwich assembly of the membrane.

FIG. 6 shows a sandwich assembly of a urethane membrane 105, plastic coated mesh 106, and a silicone sealant 104 gently pressed between the front polyethylene membrane 101 and the back polyethylene membrane 102 to knead a silicone sealant 103. The kneading of the silicone sealant 103 is squeezed into the plastic coated mesh 106 and around the edge of the urethane membrane 105. The silicone sealant forms a thin perimeter around the urethane membrane 103 roughly a $\frac{1}{4}$-inch on either side of the membrane 105 and extending out as least about $\frac{1}{8}$ inch beyond the urethane membrane's perimeter.

Figure 7:
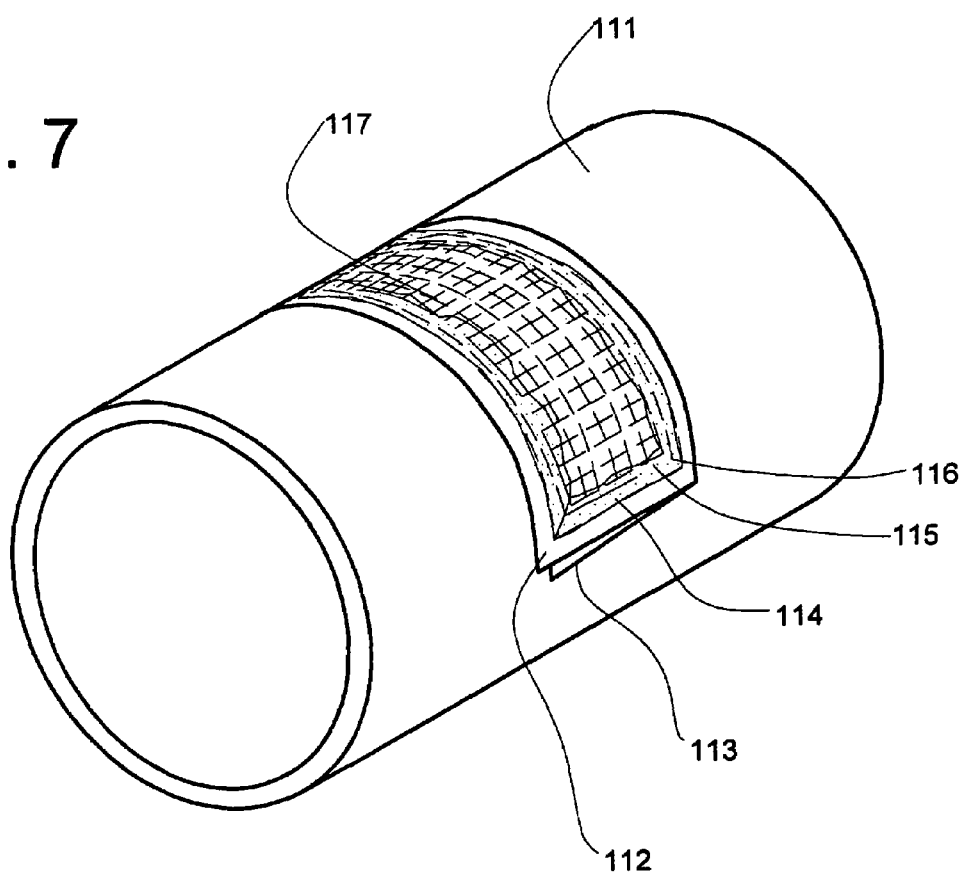
FIG. 7 shows the membrane assembly shaped as a tube.

FIG. 7 shows the membrane assembly 112, 113, 114, 115, 115, 117, which is then positioned to cure over an approximately six-inch diameter tube 111 to cure in the shape of the interior of the Plexiglas tube 17 in FIG. 2. Sprayed water is used to accelerate the cure the silicone sealant 114, 115. Once the membrane assembly 112, 113, 114, 115, 115, 117 is cured the front polyethylene cover 112 is peeled from the mesh 117 side of the membrane assembly and removed.

Figure 8:
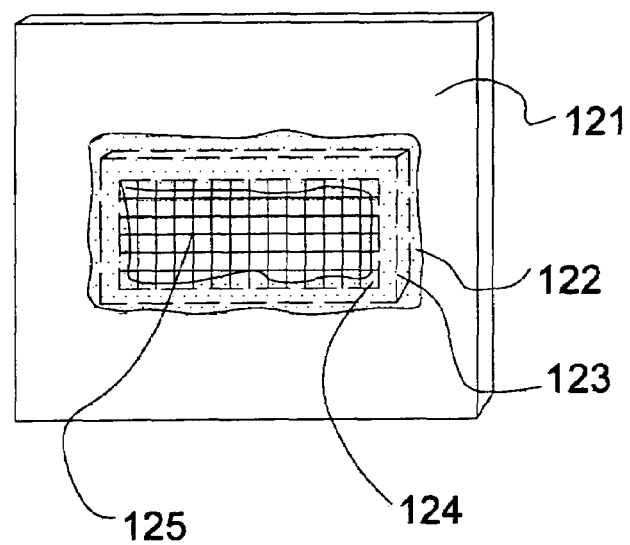
FIG. 8 shows the membrane assembly with a backing.

FIG. 8 shows the membrane assembly 122, 123, 124, 125 with the back polyethylene membrane 121. The edges of the silicone sealant skirt 122 may be trimmed to make the edges square, but preferably a minimum of about $\frac{1}{4}$ inch of a pure silicone perimeter remains.

Figure 9:
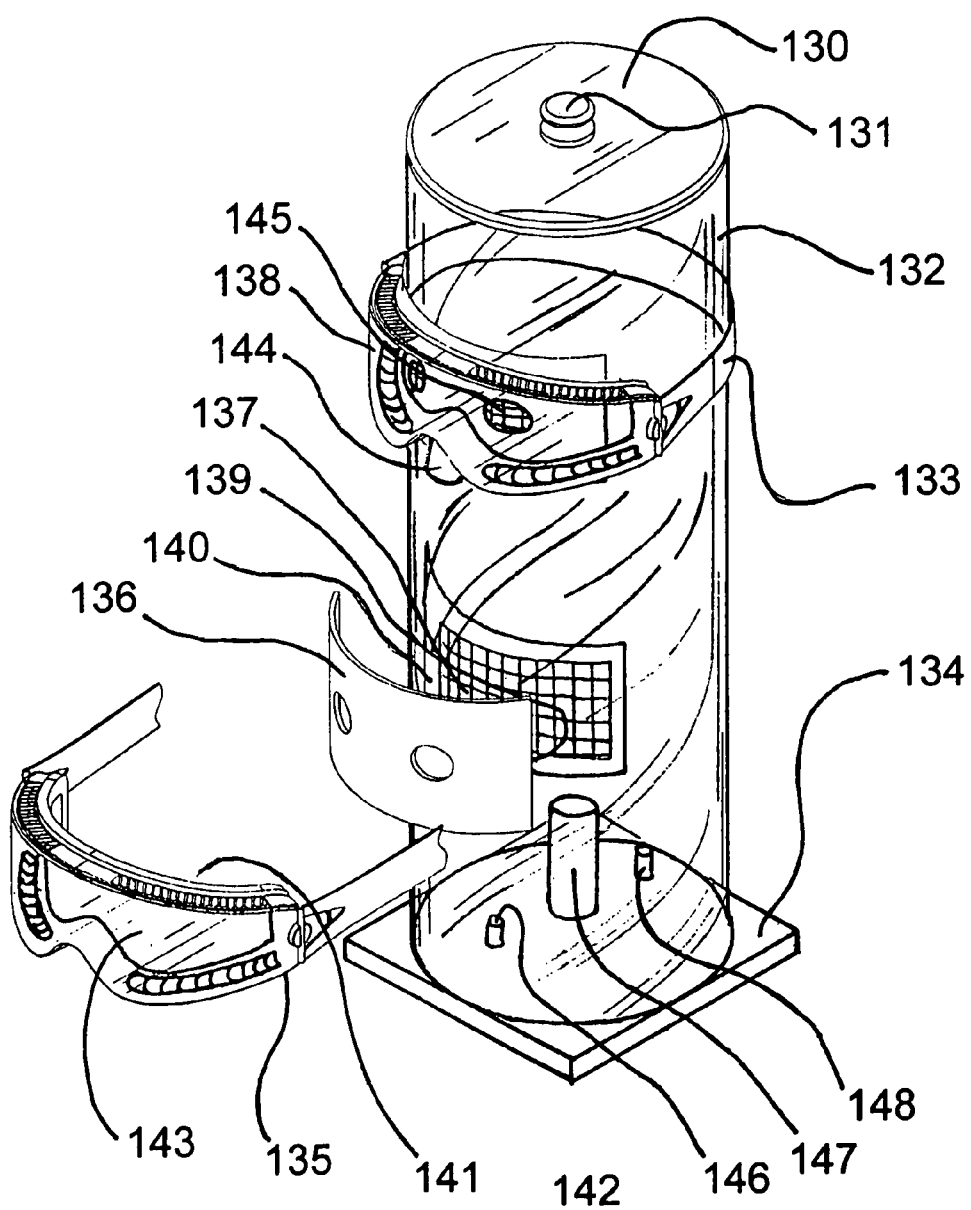
FIG. 9 is an exploded view of the lower membrane and goggles.

FIG. 9 shows lower membranes and goggles in exploded view. To mount this membrane assembly into the Plexiglas tube 132, an approximately $\frac{1}{8}$-inch diameter bead of a silicone sealant 140 is deposited around the perimeter of the port aperture 139 into the Plexiglas tube 132. The membrane assembly 137 is then mated to the silicone bead and pressed to sandwich the silicone sealant 140 onto the Plexiglas tube 132. The silicone sealant 140 is then cured and the backing polyethylene membrane 121, shown in FIG. 8, is carefully removed from the membrane assembly 137, shown in FIG. 9.

This assembly results in a urethane membrane or other membranes being held onto the Plexiglas tube 132 with sufficient mechanical support from the mesh and the sealing is sufficient to hold the water in the interior of the Plexiglas tube 132. If a leak develops in the urethane membrane assembly 137, such as a scratching or puncturing with an object, the membrane assembly can be removed from the Plexiglas tube 132 by peeling and scraping. A new membrane is then remounted onto the tube.

With a dual goggle test, care is taken to build the membranes with identical sheets of material and the area of the membrane is the same to ensure equal moisture outputs. To throttle the moisture output of the membranes into a space 141 between a lens of the goggle 135 and a membrane 137, a porous and non-water absorbing membrane such as porous polypropylene 136 is placed over the membrane assembly 137 which simulates the volume between the goggle 135 and a human face. The porous throttling membrane 136 may have apertures 142 cut into it to simulate eyes. Optical resolution patterns can also be printed onto the throttling membrane 136 to improve the viewing of fogging on the lens 143 of the goggle 135.

A second goggle 138 is shown strapped onto to the upper position on the goggle tester with the goggle strap 133. The other features of the goggle tester are the lid 130, lid knob 131, and the Plexiglas base plate 134. The air inlet 146, heater tube 147 and the thermocouple tube 148 are shown inside the Plexiglas tube 132 and extending out of the base plate 134. When the tester is operated the Plexiglas tube 132 is filled with water by removing the lid 130 by holding and lifting the lid knob 131.

For some situations the simulator may be run with the water filled below the membranes and the moist air mixed with the vigorous airflow through the air inlet 146. Other possible means of circulating the water and heat in this low water mode include spraying the water over the membrane, or forming water droplet fog within the Plexiglas tube 132. The heat transport is by convection, the vaporization and condensation of water vapor, and the moisture transport through the membranes by diffusion of the condensed water or by pervaporization where the water does not condense.

In the preferred operation, water is heated to the desired temperature and the goggles are placed onto the Plexiglas tube with the goggle making a snug fit around the Plexiglas tube 132 by tensioning the goggle strap 133 and resting the goggle on the nose piece 144 fashioned out of aluminum and Plexiglas, to seal the goggles and simulate the heat and contour of a human face and mounted to the Plexiglas tube 132. The simulator is run in a variety of air environments of temperature, relative humidity, airflow, airflow direction, snow, rain (sprays of water), and dust (such as, for example, 0.5 micron diameter Bentonite clay powder).

Transient conditions of raising or lowering the temperature of the water over a period of time in the Plexiglas tube may be done to simulate different levels of exertion of the wearer. Also, the outer environment may be changed to simulate conditions that can lead to condensation where the environment is changed for the wearer. The water condensation is observed on the lens of the goggles 143 and visually assessed.

A measurement of the amount of fogging is preferably done by mapping out the areas of the lens covered with water, calculating its area, and then dividing by the total area of the lens to obtain a percentage of the fogged area. An alternate quantitative assessment of condensation is done by allowing the goggles to build up a condensed layer of water after a measured amount of time then quickly removing the goggles and weighing the goggles. A plastic bag is used to avoid evaporation of the condensed water during the weighing. The difference in mass of the goggles before and after the condensation is a measure of water condensation. This technique of weighing the condensed moisture is also used to calibrate the membranes and the moisture delivery rate to match the simulator to the human or animal being simulated.

It is important to match moisture output of the two membranes 145, 137, 136 when the goggle tester is being used for goggle comparisons. Additional diagnostics such as temperature (thermocouple and thermistors), air flow sensors (hot wire anemometers), and humidity probes can be located in and around the goggles 138, 135 and the Plexiglas tube 132 to observe heat flows and conditions. The temperature and humidity data is useful to allow a mathematical model to calculate the heat and mass flow around the goggles.

A simple laminar flow convection and radiation heat and mass flow mathematical model predicts moisture, heat, and airflows. Predicted airflow from the geometry of fogging area percentages of a variety of modified commercially available goggles creates a correlation. For typical snow skiing conditions, if the airflow through the goggle is kept above one liter per minute, then fogging is minimal. Other environmental conditions and goggle designs are different from the typical ski goggle.

The simulator may also be used to test clothing and protection equipment (i.e., body armor, socks, and shoes).

While the invention has been described with reference to specific embodiments, modifications and variations of the invention may be constructed without departing from the scope of the invention.

The invention claimed is:

1. A method of simulating a body, the method comprising:
   controlling a temperature of a liquid in direct contact with a liquid impermeable vapor permeable membrane assembly that is attached to a tube which defines an opening that is covered by the membrane assembly;
   delivering transpiration moisture through the membrane assembly to a test item; and
   determining an effect the delivered transpiration moisture has on the test item.

2. The method of claim 1, wherein controlling the temperature comprises heating the liquid.

3. The method of claim 1, further comprising stirring the liquid.

4. The method of claim 1, wherein delivering transpiration moisture to the test item comprises delivering transpiration moisture to at least one of the following:
   an item of apparel; and
   an item of eyewear.

5. The method of claim 1, further comprising delivering other transpiration moisture through a second liquid impermeable vapor permeable membrane assembly to a second test item, wherein the second membrane assembly is attached to the tube and covers a second opening defined by the tube.

6. The method of claim 1, wherein determining the effect comprises measuring an effected area of the test item.

7. The method of claim 1, wherein determining the effect comprises:
   illuminating the membrane assembly to generate a resolution pattern on the test item; and
   utilizing the pattern to identify an effected area of the test item.

8. The method of claim 1, wherein determining the effect comprises weighing the test item.

9. The method of claim 1, further comprising controlling an environment external to the tube.

10. The method of claim 9, wherein controlling the environment comprises controlling at least one of the following:
    a temperature;
    a relative humidity;
    a rate of airflow;
    a direction of airflow;
    an amount of dust.

* * * * *